United States Patent
Udagawa et al.

(10) Patent No.: US 6,830,621 B2
(45) Date of Patent: Dec. 14, 2004

(54) LIQUID DISCHARGE APPARATUS FOR PRODUCING PROBE CARRIER, APPARATUS FOR PRODUCING PROBE CARRIER AND METHOD FOR PRODUCING PROBE CARRIER

(75) Inventors: Kenta Udagawa, Kanagawa (JP); Toshiaki Hirosawa, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 365 days.

(21) Appl. No.: 10/105,355

(22) Filed: Mar. 26, 2002

(65) Prior Publication Data

US 2002/0153435 A1 Oct. 24, 2002

(30) Foreign Application Priority Data

Mar. 28, 2001 (JP) ........................................ 2001-093265

(51) Int. Cl.⁷ ................................................ B05C 5/02
(52) U.S. Cl. ........................ 118/313; 118/315; 427/421; 422/99; 436/180
(58) Field of Search ................................ 118/313, 315; 422/99, 100, 103; 436/180; 101/366; 222/265, 266; 239/548, 555, 556; 427/421; 347/40, 43, 12

(56) References Cited

U.S. PATENT DOCUMENTS

| | | |
|---|---|---|
| 4,313,124 A | 1/1982 | Hara |
| 4,345,262 A | 8/1982 | Shirato et al. |
| 4,459,600 A | 7/1984 | Sato et al. |
| 4,463,359 A | 7/1984 | Ayata et al. |
| 4,558,333 A | 12/1985 | Sugitani et al. |
| 4,684,962 A | 8/1987 | Hirosawa et al. |
| 4,723,129 A | 2/1988 | Endo et al. |
| 4,740,796 A | 4/1988 | Endo et al. |
| 5,173,717 A | 12/1992 | Kishida et al. |
| 5,357,268 A | 10/1994 | Kishida et al. |
| 5,424,186 A | 6/1995 | Fodor et al. |
| 5,608,433 A | * 3/1997 | Quate .......................... 347/37 |
| 5,997,122 A | 12/1999 | Moriyama et al. |
| 6,284,113 B1 | * 9/2001 | Bjornson et al. ........... 204/453 |
| 6,596,237 B1 | * 7/2003 | Borrelli et al. ............. 422/100 |
| 6,656,432 B1 | * 12/2003 | Hirota et al. ............... 422/100 |
| 6,656,740 B1 | * 12/2003 | Caren et al. ................ 436/164 |

FOREIGN PATENT DOCUMENTS

| | | |
|---|---|---|
| EP | 0 703 825 | 7/1997 |
| EP | 0 895 082 | 2/1999 |
| JP | 59-123670 | 7/1984 |
| JP | 59-138461 | 8/1984 |
| JP | 11-187900 | 7/1999 |
| WO | WO 95/95505 | 12/1995 |

* cited by examiner

*Primary Examiner*—Laura Edwards
(74) *Attorney, Agent, or Firm*—Fitzpatrick, Cella, Harper & Scinto

(57) ABSTRACT

A liquid discharge apparatus for producing a probe carrier, having a configuration capable of supplying a discharge unit with plural probe solutions without increasing the dimensions of the apparatus, as well as a method and apparatus for producing the probe carrier utilizing such liquid discharge apparatus. The arrangement pitch of the supply openings to liquid holding portions from plural liquid discharging portions (which are provided in the liquid discharge apparatus and respectively correspond to the plural probes) is set to be larger than the arrangement pitch of nozzle openings, thereby increasing the freedom in designing the position and capacity of the liquid holding portions for holding the probe solutions.

13 Claims, 9 Drawing Sheets

FIG. 10
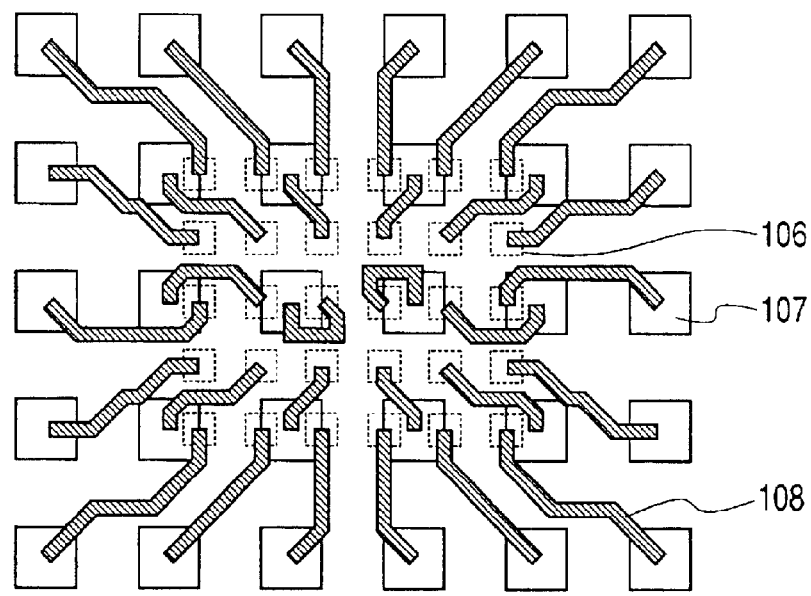
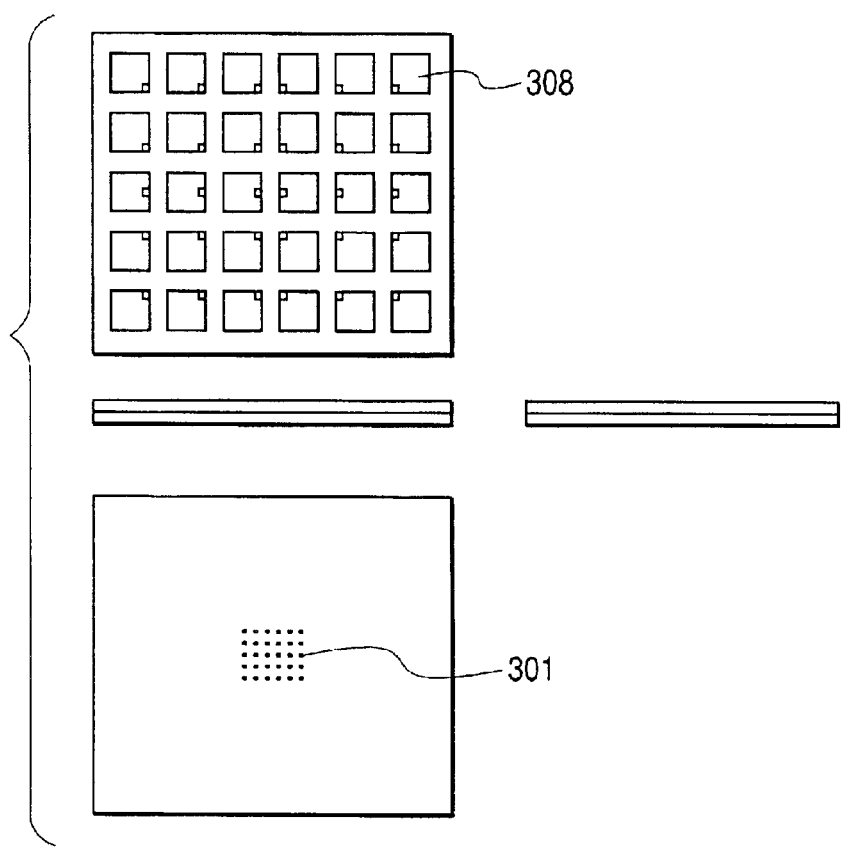
FIG. 11

LIQUID DISCHARGE APPARATUS FOR PRODUCING PROBE CARRIER, APPARATUS FOR PRODUCING PROBE CARRIER AND METHOD FOR PRODUCING PROBE CARRIER

BACKGROUND OF THE INVENTION

1. Field of the Invention

The present invention relates to a liquid discharge apparatus for producing a probe carrier having probes of plural kinds in different positions on a carrier, an apparatus for producing a probe carrier utilizing such liquid discharge apparatus, and a method for producing a probe carrier utilizing the same.

2. Related Background Art

In analyzing the base arrangement in a gene DNA or executing genetic diagnosis simultaneously on multiple items with high reliability, it is required to select the DNA of a desired base arrangement with plural probes. As means for providing the probes of plural kinds to be used for such selecting operation, so-called DNA microchip is attracting attention. Also in high throughput screening of pharmaceuticals or in combinatorial chemistry, it is required to execute systematic screening by arranging proteins or chemical solutions of plural kinds (for example 96, 384 or 1536 kinds). There are being developed methods for arraying chemical compounds of plural kinds for this purpose, automated screening technologies in such state, exclusively designed apparatuses therefor and softwares for controlling the screening operations and statistically processing the results.

Such parallel screening operation basically consists of applying so-called probe array, composed of an array of a plurality of known probes constituting selecting means, to a substance to be evaluated, thereby detecting the presence or absence of interaction or reaction with the probes under the same condition. In general, the nature of probes of which interaction or reaction is to be utilized is determined in advance, and, the probes to be mounted on a single probe array are consequently of one substance in general classification, for example a group of DNA probes with different base arrangements. For example, the substances to be utilized in a group of probes are DNA, proteins, synthesized chemical substances (pharmaceuticals) etc. In most cases, there is utilized the probe array containing a group of probes of plural kinds, but, in certain screening operations, there is utilized an array containing plural spots of DNA of the same base arrangement, protein of the same amino acid arrangement or the same chemical substance. Such array is principally utilized for example in the pharmaceutical screening.

More specifically, the probe array containing a group of probes of plural kinds usually assumes a form of arranging, on a substrate, a group of DNA's having different base arrangements, a group of proteins having different amino acid arrangements or a group of different chemical substances in an array form of a predetermined sequence of arrangement. Among such probe arrays, the DNA probe array is utilized in analyzing the base arrangement of the genetic DNA or in executing the genetic diagnosis simultaneously on multiple items with high reliability.

One of the issues in producing such probe array containing a group of probes of plural kinds is to amount the probes of as many kinds as possible, for example DNA probes of as many different base arrangements as possible, on a substrate. Stated differently, it is necessary to arrange the probes in as high density as possible.

Among the methods for fixing the probes of plural kinds in an array form on the substrate, the U.S. Pat. No. 5,424,186 discloses a method of preparing DNA probes of mutually different base arrangements in an array form, by successive DNA extending reactions utilizing photodecomposable protective radicals and photolithography on a carrier. Such method allows to prepare, for example, a DNA probe array bearing DNA probes of different base arrangements at a density of 10,000 kinds/cm$^2$ or even larger. In this method, the DNA probes of desired base arrangements are synthesized in the predetermined positions on the substrate, through the successive extending reactions, by executing a photolithographic step with an exclusive photomask for each of four bases (A, T, C and G) thereby selectively extending such bases in predetermined positions of the array. Therefore, the cost and time required for preparation increase as the DNA probe chain becomes longer. Also the proportion of the DNA probes including defects in the designed base arrangement is not small because the efficiency of nucleotide synthesis is not 100% in each extending step. Furthermore, in the finally obtained array, the proportion of the DNA probes having the designed base arrangement becomes inevitably smaller since the efficiency of synthesis is lower in the process utilizing the photodecomposable protective radicals in comparison with the ordinary process utilizing acid-decomposable protective radicals.

Furthermore, as the products synthesized directly on the carrier are to be used for the screening operation, it is naturally impossible to eliminate, from the DNA probes having designed base arrangements, those having defects in the base arrangement by a purification process. This method is also associated with a drawback that the base arrangement of the DNA probe synthesized on the substrate cannot be confirmed in the finally obtained array. This means that, in case the extension of a base is scarcely achieved in an extending step for example by an error in the process and the entire probe array becomes defective, the screening operation utilizing such defective probe array results in an erroneous result and there is no way of preventing such situation. The fact that the base arrangement cannot be confirmed is the largest and fundamental drawback of this method.

There is also proposed another method of preparing the probe array, by synthesizing and purifying the DNA for probe in advance, and, eventually after confirmation of the base length thereof, supplying each DNA onto the substrate by a suitable device such as a microdispenser. The PCT laid-open publication WO95/35505 discloses a method of supplying DNA with a capillary onto a membrane. This method in principle allows to prepare the DNA array bearing DNA probes at a density of about 1000 probes/cm$^2$. Basically this method is to prepare the probe array by supplying solution of each probe with a capillary-shaped dispensing device to a predetermined position on the substrate and repeating such operation. This method can be satisfactorily executed if an exclusive capillary is employed for each probe, but, if the number of the available capillaries is limited, it is necessary to sufficiently wash the capillary in changing the kind of probe in order to avoid mutual contamination. It is also necessary to control the supplying position at each operation. Consequently, this method is not suitable for preparing an array bearing probes of many kinds at a high density. In addition, the reproducibility and reliability are not perfect since the supply of the probe solution onto the substrate is achieved by tapping on the substrate with the end of the capillary.

There is also commercially available the microdispenser device, such as HYDRA (trade name) from Robbins Scientific Corp., for feeding solutions of different chemicals to the wells of a microplate of 96 or 384 wells, commonly utilized for the high throughput screening of pharmaceuticals. Such device basically consists of a two-dimensional array of microsyringes with a minimum discharge amount of 100 nl. If such device is applied for the array preparation, the density of the probes will be limited by such minimum discharge amount.

There is also proposed a method, in solid-phase synthesis of DNA on the substrate, of supplying the substrate with a solution of the substance required for synthesis by ink jet method in each extending step. For example, EP publication EPO 703 825B1 discloses a method of executing solid-phase synthesis of plural DNAs of respectively predetermined base arrangements by supplying a nucleotide monomer and an activator, to be utilized in the solid-phase DNA synthesis, from separate piezo jet nozzles. Such supply (coating) by the ink jet method is more reliable, for example in the reproducibility of the supply amount, in comparison with the solution supply (coating) by the aforementioned capillary, and is therefore suitable for achieving higher density of the probe array as the nozzle structure can be made finer. However, this method, basically relying on the successive DNA extending reactions on the substrate, is still associated with the largest drawback that the base arrangement of the DNA synthesized on the substrate cannot be confirmed, as in the aforementioned method disclosed in the U.S. Pat. No. 5,424,186. Though this method is relieved from the cumbersomeness that a photolithographic step involving the exclusive photomask is required for each extending step, it is still insufficient in providing the predetermined probe in each point, which is the essential condition for the probe array. Also the aforementioned EP publication 0 703 825B1 only describes the method of utilizing a plurality of singly formed piezo jet nozzles, and this method is not suitable for preparing the probe array bearing the probes at a high density in case of employing a limited number of nozzles, as in the aforementioned method utilizing the capillaries.

Also Japanese Patent Application Laid-open No. 11-187900 discloses a method of depositing a liquid containing a probe by a thermal liquid discharge unit as a liquid droplet onto a solid phase, thereby forming a spot containing the probe on the solid phase.

Also, in the biochemistry field, the probe solutions for the high throughput screening are usually prepared on a microplate which is standardized to have 96, 384 or 1536 wells with a standardized pitch between the wells. Therefore, if such microplate is applied to a liquid discharge apparatus in which the pitch of the liquid holding portions is determined by the pitch of the nozzles and does not match the pitch of wells of the microplate, there is also required an additional operation of transferring the liquids to such liquid containing portions arranged at the pitch of the discharge nozzles.

As explained in the foregoing, the known methods for preparing the probe array are still associated with various drawbacks or limitations in efficiently preparing the probe array bearing the probes of multiple kinds at a high density on the substrate. For example, in case of transferring the probe solutions synthesized on a microplate to the liquid holding portions arranged with the pitch of the nozzles in the liquid discharge apparatus with a pipette, such pipette has to be washed sufficiently in changing the kind of the probe, in order to avoid mutual contamination. Also if tubes are employed for supplying the probe solutions to the liquid discharge apparatus, the apparatus itself inevitably becomes complex and bulky if there are provided at least several hundred nozzles.

SUMMARY OF THE INVENTION

The present invention is to resolve the drawbacks in such liquid discharge apparatus for preparing the probe carrier, and an object of the present invention is to provide a liquid discharge apparatus for producing a probe carrier, allowing to supply the liquid discharge unit with the probe solutions of multiple kinds without increasing the dimension of the apparatus.

Another object of the present invention is to provide an apparatus for producing a probe carrier, allowing to supply the liquid discharge unit with the probe solutions of multiple kinds without increasing the dimension of the apparatus.

Still another object of the present invention is to provide a method for advantageously producing a probe carrier bearing probes of multiple kinds.

As a result of intensive investigation for attaining the above-mentioned objects, the present inventors have found that the supply of the probe solutions of multiple kinds to the liquid holding portions can be achieved with a simple configuration and the freedom in designing can be expanded with respect to the capacity and positioning of the liquid holding portions, by adopting, in the liquid discharge apparatus, a configuration capable of relaxing the limitation on the pitch of the liquid holding portions by the pitch of the nozzles, such as a configuration where a member in which the liquid discharge nozzles are one- or two-dimensionally arranged and a member in which the liquid holding portions to be respectively adjoined with the nozzles are one- or two-dimensionally arranged are mutually laminated.

The present invention is attained by such finding of the present inventors.

More specifically, according to the present invention, there is provided a liquid discharge apparatus for producing a probe carrier bearing, in different positions on a carrier, probes of plural kinds capable of specifically combining with a target substance, the apparatus comprising:

a liquid discharging portion, the number of which corresponds to the number of kinds of the probes, including;
1) a liquid holding portion for holding a liquid containing the above-mentioned probe;
2) a supply opening for supplying the liquid to the liquid holding portion;
3) a liquid discharging nozzle for discharging the liquid; and
4) a flow path connecting the nozzle with the liquid holding portion;
wherein the liquid discharge apparatus is provided with a nozzle opening arrangement face in which the openings of the nozzles are arranged and a supply opening arrangement face in which the liquid supply openings to the above-mentioned liquid holding portions are arranged, and the pitch of arrangement of the supply openings in the supply opening arrangement face is larger than the pitch of arrangement of the openings of the nozzles in the nozzle opening arrangement face.

The configuration of the present invention relaxes the limitation of the nozzle arrangement on the arrangement of the liquid holding portions, and increases the freedom of designing in the arrangement of the liquid holding portions, thereby allowing to provide a liquid discharge apparatus for producing a probe carrier sufficiently capable of handling the probe solutions of multiple kinds with a simple configuration.

The above-mentioned liquid discharge apparatus preferably has a configuration provided with a member including a pair of mutually opposed faces wherein the nozzle opening arrangement face is provided on one of such two faces and the supply opening arrangement face is provided on the other.

Also the liquid holding portion in the liquid discharge apparatus preferably has such a configuration as partly composed of a through hole penetrating from a face of a plate-shaped member to the other face thereof, wherein an end of the through hole is connected to the above-mentioned nozzle. Also such plate-shaped member preferably has the open end of the through hole on a face opposed to the face connected with the nozzle. Further, the through hole is preferably formed by a photolithographic process.

Also the plate-shaped member is preferably water repellent, on the face thereof where the through holes are opened, in the periphery of each opening. Furthermore, the plate-shaped member preferably has a configuration having, on the face thereof including the openings of the through holes, a groove communicating with the openings.

The liquid discharge apparatus of the present invention can assume a configuration including a liquid discharge energy generating element for liquid discharge from the nozzle. Such liquid discharge energy generating element can be composed of a heater element for generating thermal energy to heat the probe solution thereby inducing film boiling therein and causing the resulting pressure to discharge the probe solution from the nozzle opening (discharge port). Also the liquid discharging portion provided in the liquid discharge apparatus preferably has a configuration where a bubble is generated in the probe solution at the discharge of the probe solution from the nozzle by the activation of the heater element and such generated bubble communicates with the external air through the nozzle. The present invention also includes the combinations of these configurations.

According to the present invention, there is also provided an apparatus for producing a probe carrier bearing, in different positions on a carrier, probes of plural kinds capable of specifically combining with a target substance, the apparatus comprising:

A) a liquid discharge apparatus including a liquid discharging portion, the number of which corresponds to the number of kinds of the probes, provided with;

1) a liquid holding portion for holding a liquid containing the above-mentioned probe;

2) a supply opening for supplying the liquid to the liquid holding portion;

3) a liquid discharging nozzle for discharging the liquid; and 4) a flow path connecting the nozzle with the liquid holding portion;

wherein the liquid discharge apparatus is provided with a nozzle opening arrangement face in which the openings of the nozzles are arranged and a supply opening arrangement face in which the liquid supply openings to the above-mentioned liquid holding portions are arranged, and the pitch of arrangement of the supply openings in the supply opening arrangement face is larger than the pitch of arrangement of the openings of the nozzles in the nozzle opening arrangement face; and B) aligning means for aligning the relative position of the carrier and the liquid discharge apparatus.

The configuration of the present invention relaxes the limitation by the nozzle arrangement on the arrangement of the liquid holding portions, and increases the freedom of designing in the arrangement of the liquid holding portions, thereby allowing to provide an apparatus sufficiently for producing a probe carrier capable of handling the probe solutions of multiple kinds with a simple configuration.

According to the present invention, there is also provided a method for producing a probe carrier bearing, in different positions on a carrier, probes of plural kinds capable of specifically combining with a target substance, the method comprising:

A) a step of preparing a liquid discharge apparatus including a liquid discharging portion, the number of which corresponds to at least the number of kinds of the probes, provided with;

1) a liquid holding portion for holding a liquid containing the above-mentioned probe;

2) a supply opening for supplying the liquid to the liquid holding portion;

3) a liquid discharging nozzle for discharging the liquid; and 4) a flow path connecting the nozzle with the liquid holding portion;

wherein the liquid discharge apparatus is provided with a nozzle opening arrangement face in which the openings of the nozzles are arranged and a supply opening arrangement face in which the liquid supply openings to the above-mentioned liquid holding portions are arranged, and the pitch of arrangement of the supply openings in the supply opening arrangement face is larger than the pitch of arrangement of the openings of the nozzles in the nozzle opening arrangement face; and B) a step of discharging the liquid containing the probe onto the different positions on the carrier from the liquid discharge apparatus.

The present invention allows to provide a method of advantageously producing a probe carrier bearing probes of multiple kinds.

BRIEF DESCRIPTION OF THE DRAWINGS

FIG. 10 is a see-through view showing the arrangement of the liquid flow paths in the liquid discharge unit of the second embodiment of the present invention;

FIG. 11 is a view showing the liquid discharge unit in a third embodiment of the present invention;

DESCRIPTION OF THE PREFERRED EMBODIMENTS

In the following, the liquid discharge apparatus of the present invention will be explained in detail with reference to the accompanying drawings.

Figure 1:
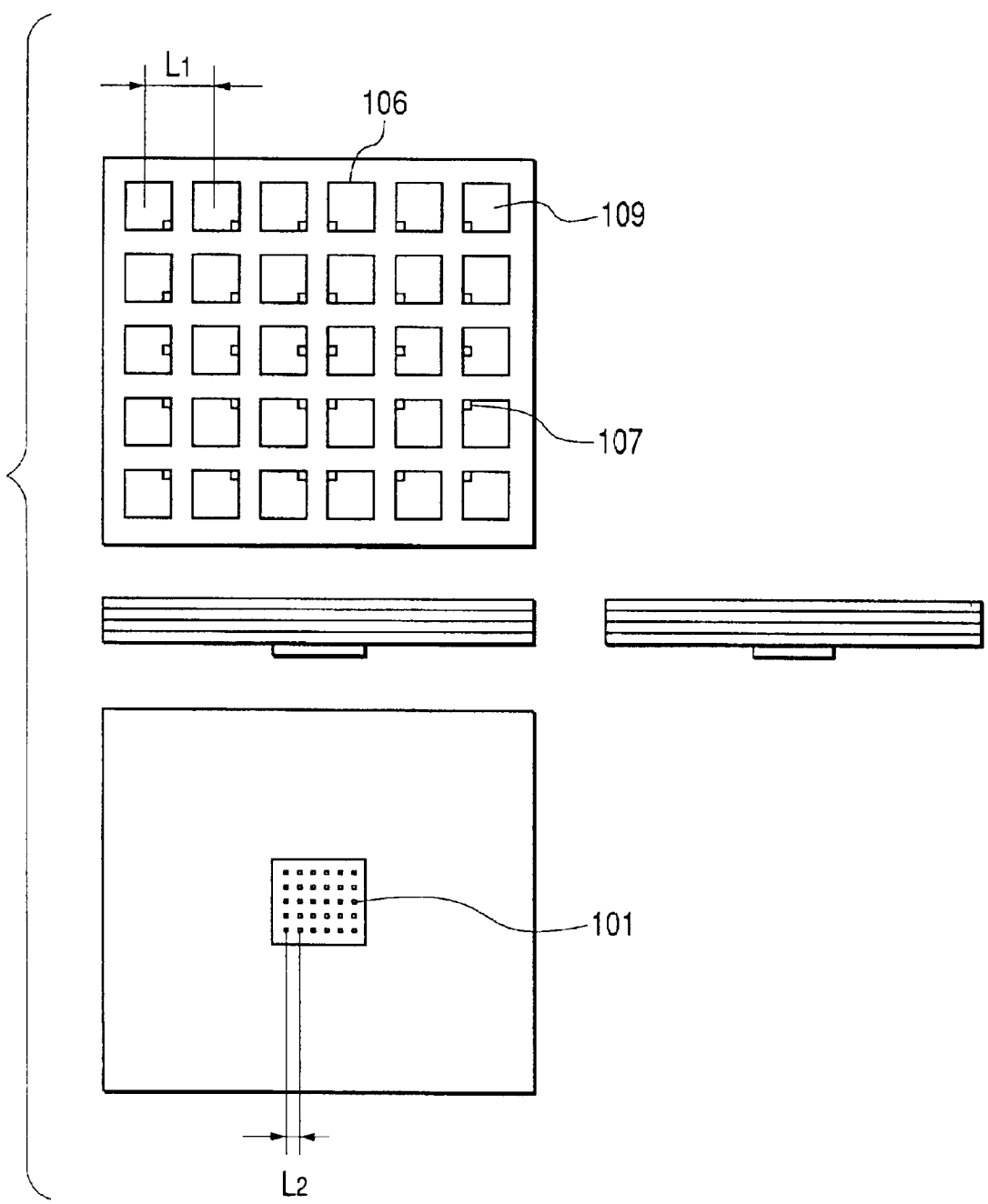
FIG. 1 is a view showing an embodiment of the liquid discharge apparatus of the present invention.

FIG. 1 is a view showing the liquid discharge apparatus constituting an embodiment of the present invention.

The liquid discharge apparatus is provided with liquid holding portions 109 for holding liquids containing probes, supply openings 106 for supplying the liquid holding portions with probe solutions, liquid discharging nozzles, and flow paths 107 for connecting the nozzles and the liquid holding portions.

The liquid discharge apparatus of the present invention has such a configuration that the liquid holding portions are arranged with a pitch larger than that of arrangement of the nozzle openings.

The pitch of arrangement of the nozzle openings means the distance between the centers of the two adjacent nozzles, arbitrarily selected from the nozzles arranged in a one-dimensional or two-dimensional array.

Also the pitch of arrangement of the supply openings for supplying the liquid holding portions with the probe solutions means the distance of the supply openings in the two liquid holding portions connected with such arbitrarily selected two nozzles. Such distance is measured in the adjacent liquid holding portions between two points in the same positions on the two supply openings. For example, the distance of the centers of the two supply openings in an arbitrarily selected direction can be regarded as the pitch of arrangement.

Referring to FIG. 1, liquid reservoirs 109 constituting the liquid holding portions have square openings on the opening face, so that the square openings of the same size are repeatedly arranged with the same pitch in two-dimensional manner. In the example shown in FIG. 1, a row in the horizontal direction contains six liquid reservoirs and such row is arranged in five units in the vertical direction. On the other hand, the openings 101 of the nozzles connected to such liquid reservoirs 109 are arranged in a similar two-dimensional arrangement on the nozzle arrangement face. As shown in FIG. 1, the arrangement pitch L1 (based on the centers of the openings) of the liquid reservoirs 109 set to be larger than the arrangement pitch L2 of the nozzle openings.

However, the arrangement of the supply openings need not be the same as that of the nozzle openings.

Figure 5:
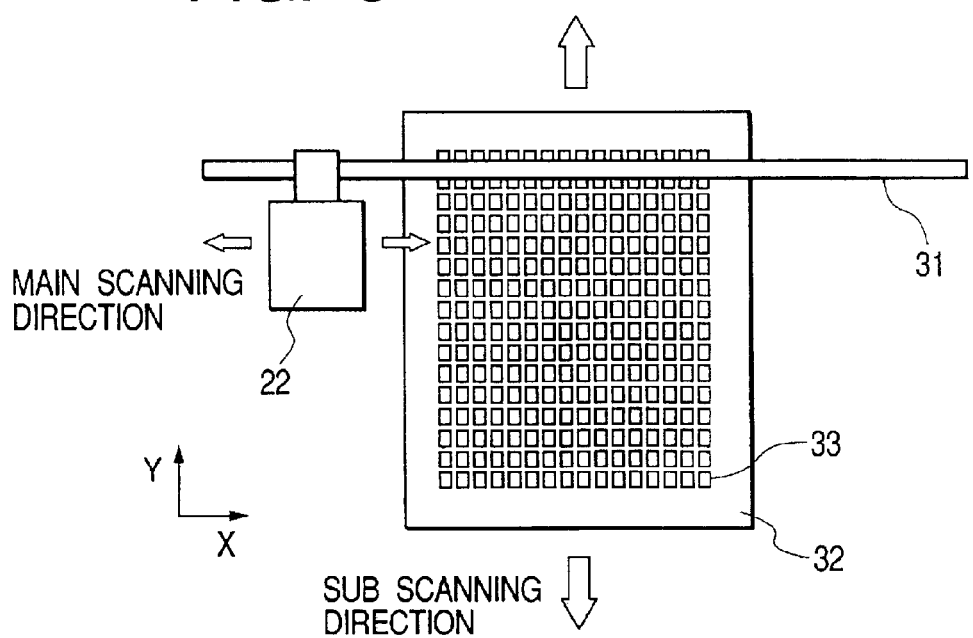
FIG. 5 is a view showing an embodiment of the probe carrier producing apparatus of the present invention.

For example, there can be advantageously adopted a configuration where the supply openings are arranged with an arrangement pitch on an orthogonal coordinate system as shown in FIG. 1 so as to match the commercially available microplate while the nozzles are arranged, as shown in FIG. 5, in such a manner that a nozzle group consisting of plural nozzles arranged in the horizontal direction is positioned with a predetermined distance with an offset to the adjacent nozzle group.

Such "offset" means an arrangement in which the positions of the nozzles constituting a nozzle row are mutually shifted between the adjacent nozzle rows. For example in an example shown in FIG. 4, in the first nozzles from the left-hand end in the horizontally extending nozzle rows, such first nozzle in the second row from the top is positioned with a displacement of a certain distance to the left, with respect to the first nozzle in the first row positioned directly above. Similarly, the first nozzles in the third to fifth rows are positioned with similar displacements of the same distance to the left. Since the nozzles within each row have a constant pitch, the second to eighth nozzles in the different rows are similarly arranged with the predetermined displacements. In the shifted arrangement in the example shown in FIG. 4, no nozzles mutually overlap in the main scanning direction (moving direction of the discharge apparatus), so that it is rendered possible to effectively increase the density, in the lateral direction in FIG. 4, of the spots formed on the solid substrate by the probe solutions discharged from the respective nozzle rows.

The effect of the present invention advantageously becomes more evident in an embodiment requiring a liquid discharge apparatus provided with the paired solution reservoir and nozzle in at least 100 sets, corresponding to the number of kinds of the probes to be borne on the produced probe carrier. The present invention is preferably employed in an embodiment requiring a liquid discharge apparatus provided with the paired solution reservoir and nozzle in at least 1,000 sets, and more preferably in an embodiment requiring a liquid discharge apparatus provided with the paired solution reservoir and nozzle in at least 10,000 sets. Furthermore, the present invention may be exploited in an embodiment requiring a liquid discharge apparatus provided with the paired solution reservoir and nozzle in at least 100,000 sets.

It is also preferable to prepare the nozzles in a number larger than the necessary number of kinds of the probes, in consideration of possibility of causing discharge failure in the nozzles.

In case of employing the liquid discharge apparatus provided with nozzles of such large number, the area density of the nozzles is preferably equal to the density of the desired probe carrier in consideration of the aforementioned alignment of the discharge positions. For example by employing the liquid discharge apparatus with 100 nozzles/$cm^2$ or higher, 1000 nozzles/$cm^2$ or higher, or 10000 nozzles/$cm^2$ or higher, the probe solutions can be discharged onto the carrier with a corresponding high density without requiring alignment of the discharge position of each nozzle.

However, in the liquid discharge apparatus provided with the nozzles in such high density, it is determined, according to the required amount of the probe solution, whether separate solution holding portions are to be mounted in addition to the liquid reservoirs 109. The determination depends also on the structure of the discharge apparatus, and the supply method of the probe solutions to the liquid reservoirs 109.

Normally, the liquid holding portions are preferably formed by the repetition of the same planar form from the standpoint of the producing method therefor and the designing of the liquid discharge apparatus. The planar shape of the aperture of the liquid holding portion may assume various shapes such as circular, oval or rectangular shape according to the producing method.

For forming the arrangement pitch of the liquid holding portions larger than that of the nozzle openings, there is advantageously employed a configuration in which a member bearing the nozzles and a member bearing the liquid holding portions are adjoined in a laminar manner through an intermediate member as required.

For such laminar structures there is preferred a configuration in which a liquid supplying plate formed as a plate-shaped member in which the liquid holding portions are arranged is adjoined to a heater board formed as a plate-shaped member and bearing heater elements as the discharge energy generating means for liquid discharge from the nozzle openings.

The liquid supply plate is required to assist dissipation of the heat generated by the heater board at the discharge of the probe solutions, and is also required to have satisfactory liquid contact properties not detrimentally affecting the probe solutions.

Also, if the heater board and the liquid supply plate show a large difference in the thermal expansion coefficient, there may result peeling, cracking or deformation in the adjoining portion between the heater board and the liquid supply plate depending on the thermal hysteresis after direct adjoining thereof. Therefore, the plate-shaped member constituting the liquid supply plate is preferably composed of the same material as that of the substrate portion of the heater board or that having a similar thermal expansion coefficient thereto. For example, in case the heater board is composed of a silicon substrate, the liquid supply plate may be composed of alumina ceramics in consideration of the thermal expansion. In case the heater board and the liquid supply plate are different in the thermal expansion coefficient and an adhesive is employed for the adjoining thereof, there is preferably employed an adhesive with elasticity. Also the difference in the thermal expansion coefficient may be disregarded in case an elastic member such as chlorinated butyl rubber is sandwiched between the heater board and the liquid supply plate, and, in such case, there may be employed glass or thermoplastic resins in consideration of the liquid contact property or the ease of working.

Furthermore, in consideration of the supply operation of the probe solutions to the liquid supply plate, the arrangement of the probe solution supply openings provided in the liquid supply plate is preferably set into the same one as that of the wells in the ordinarily employed microplate, whereby the probe solutions prepared in the wells of the microplate can be efficiently provided to the supply openings of the liquid supply plate. Also there can be utilized the ordinarily available microplate and the related apparatuses in the preparation of the probe solutions and the supply thereof to the liquid supply plate.

The arrangement pitch of the nozzle openings by no means limits the present invention but can be selected for example within a range of 10 $\mu$m–2 mm, and the arrangement pitch of the supply openings can be for example 9, 4.5 or 2.25 mm.

For example a liquid discharge apparatus having an arrangement pitch of the nozzle openings of 160 $\mu$m and an arrangement pitch of the supply openings of 9 mm enables easy supply of the probe solutions from the commercially available microplate supply apparatus and can produce a probe carrier bearing the probe solutions at a density of 158.75 dpi without requiring relative displacement between the liquid discharge apparatus and the carrier.

In the present specification, the probe fixed on the carrier is capable of specific combination with a specified target substance. Such probe contains an oligonucleotide, a polynucleotide or another polymer recognizable by the specified target substance. The term "probe" means both a molecule with a probe function such as the individual polynucleotide module and a group of molecules of the same probe function such as polynucleotide molecules of the same molecular arrangement fixed in dispersed positions on the surface, and also includes a molecule which is often called ligand. Also the terms probe and target are often interchangeably utilized, and the probe means a substance capable of combining with the target or capable of becoming combinable with the target as a part of a ligand-antiligand (also called receptor) pair. Also the probe and the target in the present invention may include a base found in the nature or substances similar thereto.

As an example of the probe to be supported on the carrier, there can be employed an oligonucleotide having a base arrangement capable hybridization with the target nucleic acid, also partly having a combining portion through a linker and having a structure connected to the carrier surface in the combining portion with the carrier. The probe is, preferably, a single-strand nucleic acid having a complementary base sequence to all or a part of the target nucleic acid, the probe can be hybridized specifically with the target substance. In case of such structure, the position of the combining portion with the carrier within the oligonucleotide molecule is not particularly limited within a range not hindering the desired hybridization reaction.

The probe to be employed in the probe array to which the method of the present invention is applicable can be suitably selected according to the purpose of use of the probe array, but, for advantageously exploiting the method of the present invention, the probe is preferably at least one selected from DNA, RNA, cDNA (complementary DNA), PNA, oligonucleotide, polynucleotide, other nucleic acids, oligopeptide, polypeptide, protein, enzyme, base substance thereto, antibody, epitope thereto, antigen, hormone, hormone receptor, ligand, ligand receptor, oligosaccharide and polysaccharide.

In the present invention, the probe carrier means a carrier surfacially bearing such probes of plural kinds fixed in respective independent areas for example as dot-shaped spots, and the probe array means a planar or two-dimensional array of the multiple probe spots. Such probe carrier includes plates and chips for inspection generally called DNA macroarray, DNA chip or probe array.

On the other hand, it is desired that the probe is provided with a structure capable of combining with the carrier surface and the fixation of the probe to the carrier is achieved through such combinable structure. In such configuration, the structure capable of binding to the carrier surface, which the probe has, is preferably one which has been formed by treatment for introducing previously to a molecular of a probe material at least one of organic functional groups, such as an amino group, a mercapto group, a carboxyl group, a hydroxyl group, an acid halide (a haloformyl group: —COX), a halide (—X), an aziridine group, a maleimide group, a succinimide group, an isothiocyanate group, a sulfonyl chloride (—SO$_2$Cl) group, an aldehyde group (formyl group: —CHO), hydrazine, and iodinated acetamide. In this case, it is necessary to previously introduce onto the surface of the substrate a structure (an organic functional group) which reacts with each of various types of the above mentioned organic functional groups to form covalent bonding.

In this case, it is necessary to previously introduce onto the surface of the substrate a structure (an organic functional group) which reacts with each of various types of the above mentioned organic functional groups to form covalent bonding. For example, when the probe material has an amino group, succinimide ester, isothiocyanate, sulfonylchloride and aldehyde can be introduced onto the surface of the substrate. When the probe material has mercapto group (thiol group), maleimide can be introduced onto the surface of the substrate. When glass material is used as the substrate, a required functional group can be introduced onto the surface of the substrate by using a silane coupling agent having the required functional group, and additionally a crosslinker having the required functional group.

Also the components to be employed in the liquid discharge apparatus of the present invention or in the probe carrier producing apparatus utilizing such liquid discharge apparatus may be suitably selected or modified in structure, according to the object of the present invention, from those employed in the ink jet recording method for printing or in the recording head or recording apparatus utilizing such method. Among various ink jet printing systems, the present invention brings about excellent effects particularly in a printing head or a printing device of the type provided with means for generating thermal energy (such as electrothermal converting member or laser beam) to be used for discharging ink and adapted to induce a state change of the liquid by such thermal energy, since such system can achieve a higher density and a higher definition of the recorded image.

As to its representative configuration and principle, for example the one practiced by the use of the basic principle disclosed in the U.S. Pat. Nos. 4,723,129 and 4,740,796 is preferred. This system is applicable to either of the so-called on-demand type and the continuous type. Particularly is the case of the on-demand type it is effective, because applying at least one driving signal which gives rapid temperature elevation exceeding nucleus boiling corresponding to the recording information on an electrothermal converting member arranged corresponding to the sheets or liquid channels holding liquid generates thermal energy at the electrothermal converting member to induce film boiling at the heat action surface of the printing head, and a bubble can be consequently formed in the liquid (ink) corresponding one-to-one to the driving signals. By discharging the liquid (ink) through a discharge opening by the growth and shrinkage of the bubble, at least a droplet is formed. By forming the driving signals into pulse shapes, growth and shrinkage of the bubble can be effected instantly and adequately to accomplish more preferable discharging of the liquid (ink) particularly excellent in the response characteristics. As the driving signals of such pulse shapes, those disclosed in the U.S. Pat. Nos. 4,463,359 and 4,345,262 are suitable. Further excellent recording can be performed by employment of the conditions described in the U.S. Pat. No. 4,313,124 of the invention concerning the temperature elevation rate of the above-mentioned heat action surface.

As the configuration of the printing head, in addition to the combinations of the discharging orifice, liquid channel and electrothermal converting member (linear liquid channel or right-angled liquid channel) as disclosed in the above-mentioned respective specifications, the configuration by the use of the U.S. Pat. Nos. 4,558,333 and 4,459,600 disclosing the configuration having the heat action portion arranged in the flexed region is also included in the present invention. In addition, the present invention can also be effectively applied to the configuration of the Japanese Patent Application Laid-open No. 59-123670 using a slit common to a plurality of electrothermal converting members as the discharging portion of the electrothermal converting members or of the Japanese Patent Application Laid-open No. 59-138461 having the opening for absorbing a pressure wave of thermal energy corresponding to the discharging portion. This is because the present invention can achieve secure and efficient recording, regardless of the configuration of the printing head.

Furthermore, the present invention is effectively applicable to the recording head of the full line type having a length corresponding to the maximum width of the printing medium which can be recorded by the printing device, and such printing head may have a configuration realizing such length by the combination of plural printing heads, or a configuration constituted by an integrally formed single printing head.

In addition, the present invention is effective, within the printing devices of the serial type mentioned above, in a printing head fixed to the main body of the printing device, or an exchangeable chip-type printing head enabling electrical connection with the main body of the printing device or liquid supply from such main body by being mounted on the main body, or the printing head of a cartridge type in which a liquid tank is integrally provided in the printing head itself.

Also in the configuration of the recording device of the present invention, the addition of discharge restoration means for the printing head, preliminary auxiliary means etc. is preferable, because the effect of the present invention can be further stabilized. Specific examples of these may include, capping means, cleaning means, pressurization or aspiration means, preliminary heating means for effecting heating by an electrothermal converting member, another heating element or a combination thereof, and preliminary discharge means for effecting an idle discharge independent from that for printing.

For the aforementioned liquid, the most effective one is the type utilizing the aforementioned film boiling.

In the following there will be given a detailed explanation on the method of producing a probe carrier by a discharge apparatus of a system inducing a state change of solution by thermal energy (thermal jet system), but the discharge method is not limited to such system and the present invention can also be realized in the piezo jet system for discharging liquid by a deformation of a piezo element resulting a voltage application thereto.

Probe Carrier Producing Apparatus

In the following, an apparatus of the present invention for producing a probe carrier will be explained in detail.

FIG. 5 is a schematic view of a probe carrier producing apparatus of the present invention. As shown in FIG. 5, the apparatus of the invention has alignment means (moving means 31 for moving a liquid discharge apparatus 22 in the main and sub scanning directions) for mutual alignment of a carrier 33 and the liquid discharge apparatus 22. The alignment means may be a stage 32 that moves in the main and sub scanning directions or may have such a constitution that the apparatus of the invention is moved in the main scanning direction by the liquid discharge apparatus moving means 31 and the stage 32 is moved in the sub scanning direction.

In the following, there will be detailedly explained the method of producing a probe carrier, utilizing such apparatus.

Probe Carrier Producing Method

In the following there will be explained the method of producing the probe carrier with the above-described liquid discharge apparatus.

In an embodiment of the probe carrier producing method of the present invention, in producing a two-dimensional probe carrier, the probes separately prepared in advance are formed in solutions and are discharged and coated by desired amounts on the substrate surface by a liquid discharge apparatus provided with nozzles arranged in a predetermined array, thereby achieving a high density array of probes of multiple kinds.

In the use of the liquid discharge apparatus provided with the nozzle openings arranged in a two-dimensional array, there can be adopted following modes on the arrangement of nozzles and the control thereof.

a) A configuration where the liquid discharge apparatus of the present invention is constructed as a chip and the heater elements corresponding to the n nozzles belonging to the same column are commonly connected to a first and second wirings; or b) A configuration where the nozzle openings are arranged in a two-dimensional array, while the nozzles in each chip are arranged in a two-dimensional array consisting of m rows and n columns, the heater elements corresponding to the m nozzles belonging to the same column constitute a heater group commonly connected to the first and second wirings, and the heater groups are driven in succession in desired timings.

In the above-mentioned configuration a) or b), the nozzle density in the liquid discharge apparatus is preferably set to be the same as the probe density on the probe array. In such producing method, no scanning operation is required in the liquid discharge apparatus in producing a single probe array.

c) A configuration where the nozzle openings are arranged in a two-dimensional array, the nozzles in each chip are arranged in a two-dimensional array with m rows and n columns, and a nozzle group of X-th row ($1 \leq X \leq n$) consisting of m nozzles is positioned with an offset with respect to the adjacent nozzle groups.

d) A configuration where the nozzle openings are arranged in a two-dimensional array, the nozzles in each chip are arranged in a two-dimensional array with m rows and n columns, and a nozzle group of X-th row ($1 \leq X \leq n$) consisting of m nozzles and having a distance Y between the adjacent nozzles is positioned with an offset of a distance of Y/n with respect to the adjacent nozzle groups.

e) A configuration where the nozzle openings are arranged in a two-dimensional array, the nozzles in each chip are arranged in a two-dimensional array with m rows and n columns, and a nozzle group of X-th row ($1 \leq X \leq n$) consisting of m nozzles is positioned with a distance Z to an adjacent nozzle group, wherein the nozzle group of the adjacent column executes discharge at a timing of displacement of the liquid discharge apparatus by a distance Z after the discharge from the nozzle group of the X-th column.

In the above-mentioned configuration c), d) or e), the probe solutions can be discharged into the solid substrate with a density higher than the nozzle density of the liquid discharge apparatus, by controlling the timing and pattern of the liquid discharge.

In the following there will be explained in detail the method for producing the probe carrier utilizing the aforementioned configurations.

Method for Producing a Probe Carrier Bearing Probes at the Same Density as the Nozzle Density In the following there will be explained an example of the method for producing the probe array, with reference to the accompanying drawings. At first there will be explained the method for discharging the probe solutions with the liquid discharge apparatus of a thermal jet system shown in FIG. 1.

As shown in FIG. 1, the chip of the discharge apparatus is provided with nozzles arranged in five columns in the vertical direction and six rows in the horizontal direction and with an arrangement pitch of 160 μm between the adjacent nozzles. Since the heaters of all the nozzles are commonly connected to the first and second aluminum wirings, the liquid discharge can be induced in all the nozzles by applying a voltage pulse between a pair of electrode pads connected to these wirings. Stated differently, in response to the application of the voltage pulse, the liquid discharge simultaneously takes place in 30 nozzles.

The simultaneous discharges from all the nozzles form 30 probes on the carrier.

In this operation, the center-to-center distance between the adjacent probes is 160 μm (corresponding to 158.75 dpi).

As explained in the foregoing, the liquid discharge apparatus shown in FIG. 1 can produce a probe carrier bearing probes in 6 rows and 5 columns with a density of 158.75 dpi.

Also from the foregoing description, it will be easily understood that a probe array bearing a larger number of probes can be produced by a similar configuration.

The chip constituting the liquid discharge apparatus of the present invention may assume a simple structure consisting of heaters and wirings connected thereto, and need not be composed of a silicon substrate but can be composed of a less expensive substrate such as a glass substrate.

In the foregoing, there has been explained a liquid discharge apparatus composed of a semiconductor chip in which 30 nozzles are arranged in 6 rows and 5 columns, but the number of the nozzles and the arrangement thereof are not limited to those in the foregoing embodiment but can be selected in arbitrary manner.

Figure 6:
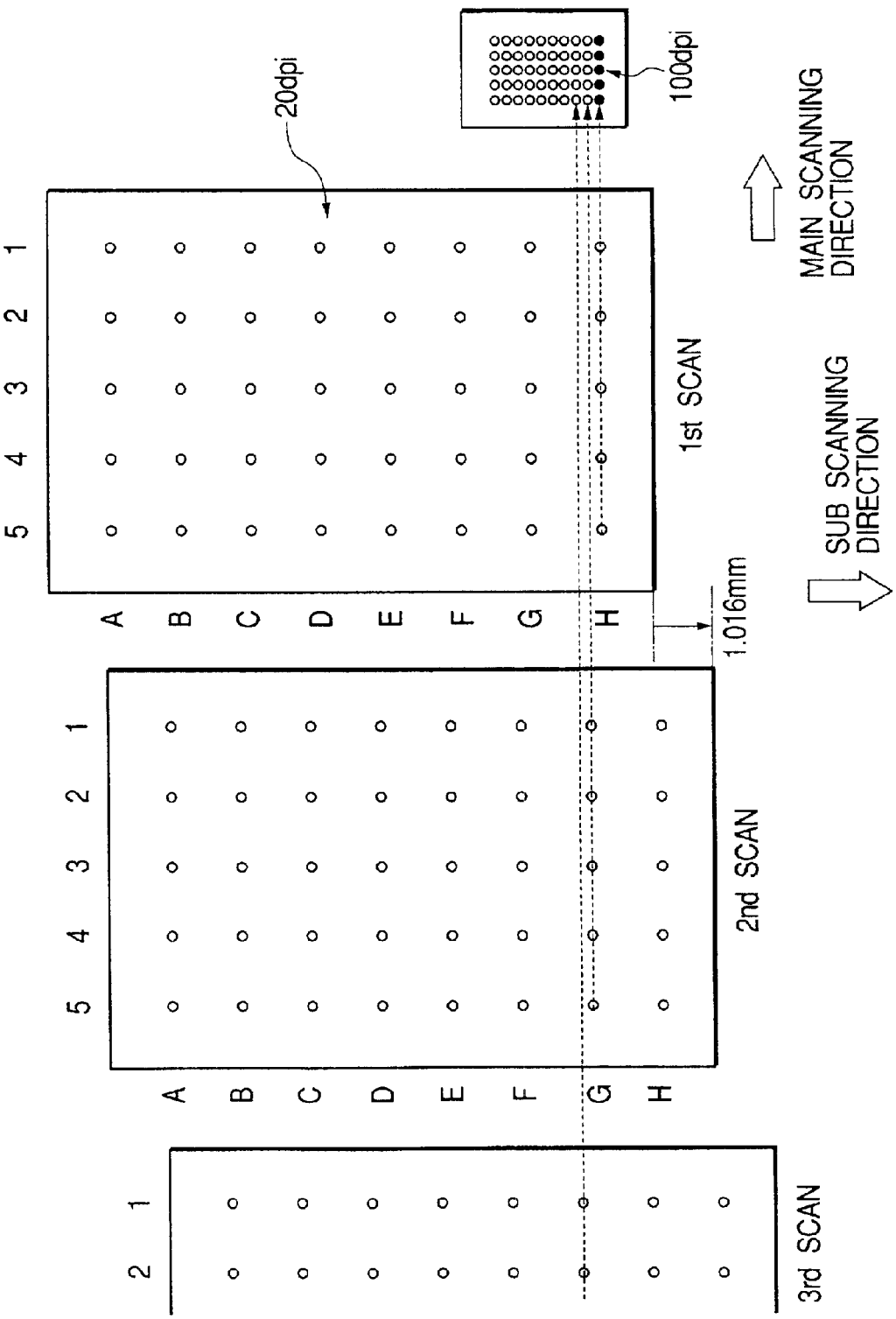
FIG. 6 is a view showing an embodiment of the probe carrier producing method of the present invention.

In case of preparing a liquid discharge apparatus of one-dimensional configuration such as 1 row by 25 columns utilizing the semiconductor chip explained in the foregoing embodiment, the probe array can be produced by only the main scanning motion so that the probe array producing apparatus can be made simpler than that shown in FIG. 6.

In case the discharge apparatus is composed of a single chip, the production yield can be maintained high even for an increased chip size, so that it is also possible to prepare a chip with a larger number of nozzles, for example 1000 nozzles.

If a probe array bearing 1000 probes is to be produced with such chip, there can be dispensed with the operation of adjoining plural chips with mutual alignment to the member of the liquid discharge apparatus, which thus can be produced with a simple structure.

Also the heaters corresponding to the nozzles may be made independently controllable. In such case, such heaters may be driven in successive manner or at the same time.

Also the liquid discharge apparatus may be prepared with plural chips.

Another Method for Discharging Probe Solutions with a Liquid Discharge Unit of a Thermal Jet System In the following there will be explained another discharging method for producing the probe array.

In the following illustration of the discharging method, the arrangement of the nozzle openings alone will be schematically shown for the purpose of simplicity, and the arrangement of the supply openings and the reservoirs will be omitted.

In the following there will be explained a method for producing a probe array bearing probes at a density higher than the nozzle density, utilizing a liquid discharge apparatus of a nozzle arrangement as shown in FIG. 6. The nozzle density is assumed to be 20 dpi, corresponding to a distance of 1.27 mm between the adjacent nozzles, and such discharge apparatus is utilized in producing a probe array with a probe density of 100 dpi. FIG. 6 shows the method for producing the probe array of 100 dpi with a chip of 20 dpi.

Figure 4:
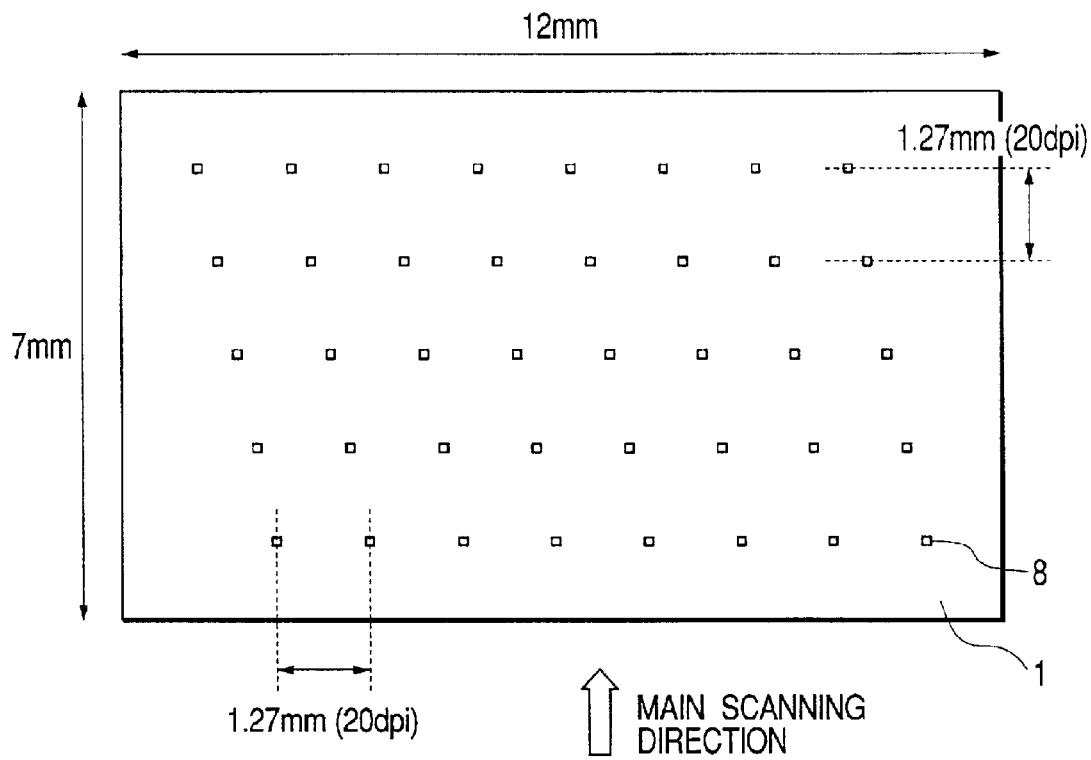
FIG. 4 is a schematic view showing an embodiment of the liquid discharge apparatus of the present invention.

Since the probe pitch of the probe array is 100 dpi while the nozzle pitch is 20 dpi, the probes cannot be formed in a single discharge operation. Therefore, in case of employing a chip with a nozzle arrangement of 8 rows by 5 columns as shown in FIG. 4, the probe array is produced by repeating 8 discharge operations in total.

In a single discharge operation, the liquid discharge apparatus is moved in a scanning motion in a direction indicated by an arrow (main scanning direction), and the heaters are driven when the nozzles in 5 columns respectively pass through predetermined positions (corresponding to 100 dpi) to form a probe row in which the probes are arranged in the horizontal direction at a density of 100 dpi.

Black circles (●) indicate the probes discharged in the first scanning motion, which thus forms the probes of the first row (from the bottom) in the probe array. Then the head is shifted by 1.016 mm in the sub scanning direction as illustrated, and the discharge operation is conducted in the same manner as in the first discharge operation. In this manner 5 probes are prepared in each scanning motion, and the discharge operation is repeated with the displacement of the liquid discharge head in the vertical direction to produce 8 probes arranged at a density of 100 dpi in the vertical direction.

In the foregoing, there has been explained the method of producing the probe array of 8 rows by 5 columns with a probe pitch of 0.254 mm (100 dpi) utilizing the chip with the nozzle arrangement of 8 rows by 5 columns with a nozzle pitch of 1.27 mm (20 dpi), but the number and arrangement of nozzles or probes are not restrictive and there can be produced a probe array with an arbitrary number of probes by a similar process. Also in case of arranging the probes as explained above, the probes have to be discharged from the respective nozzles at respectively desired timings, so that the heaters corresponding to the nozzles are made independently controllable. More specifically, there is preferred a wiring configuration in which ends of the heaters are connected to a common wiring while the other ends thereof are independently extracted.

The producing method of the present embodiment allows to reduce the relative moving distance between the carrier and the discharge apparatus in comparison with the case of utilizing the liquid discharge apparatus with the nozzle arrangement of the same pitch as that of the supply openings. Such method is therefore economical in energy and in cost, and is therefore capable of improving the throughput and reducing the cost.

Method for Producing a Probe Carrier with a Liquid Discharge Apparatus with Offset Nozzle Arrangement In the following there will be explained another example of the method for producing the probe array.

In the following illustration of the discharging method, the arrangement of the nozzle openings alone will be schematically shown for the purpose of simplicity, and the arrangement of the supply openings and the reservoirs will be omitted.

Figure 7:
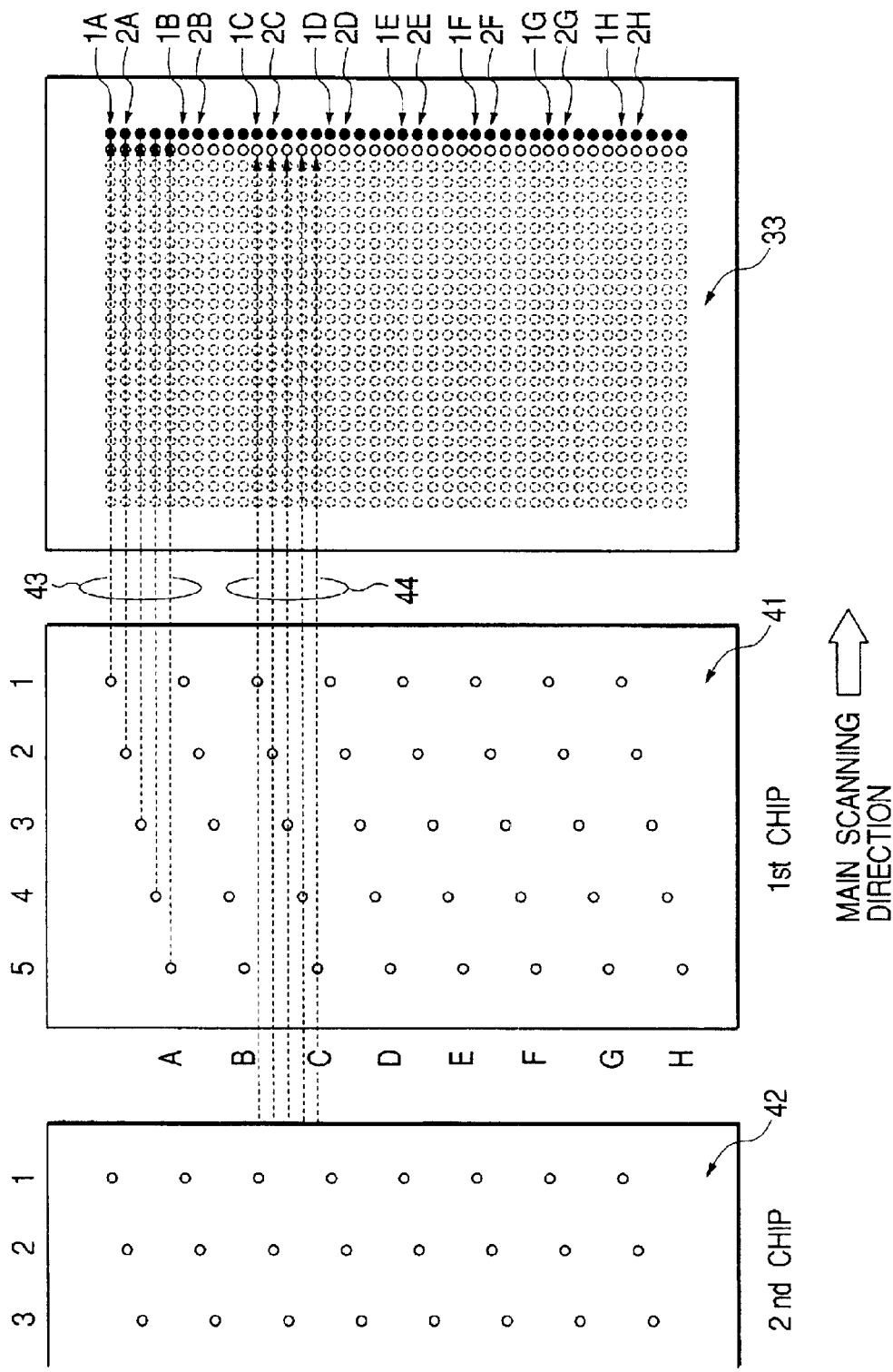
FIG. 7 is a view showing another embodiment of the probe carrier producing method of the present invention.

FIG. 7 is a schematic view showing the discharge method for the probe solutions by a liquid discharge apparatus of a thermal jet system, wherein shown are liquid discharge apparatus 41, 42 composed of semiconductor chips and a probe array 33.

Referring to FIG. 7, each chip is provided with nozzle groups each of which is composed of 8 nozzles and is positioned with an offset with respect to the adjacent nozzle groups. The heaters within each nozzle group are commonly connected to a first and second aluminum wirings as explained in the foregoing, so that the liquid discharge can be induced simultaneously in the nozzles constituting the same nozzle group, by applying a voltage pulse between a pair of electrode pads connected to these wirings. Stated differently, in response to the application of a voltage pulse, the liquid discharge takes place in 8 nozzles at the same time.

In FIG. 7, numerals 1, 2, 3, 4 and 5 adjacent to the chip indicate the nozzle groups, and characters A, B, C, D, E, F, G and H indicate the individual nozzles constituting each nozzle group.

At first the first nozzle group forms 8 probes indicated by 1A, 1B, 1C, 1D, 1E, 1F, 1G and 1H shown in FIG. 7. Then, when the liquid discharge apparatus is moved in the main scanning direction by 1.27 mm (corresponding to 20 dpi), the second nozzle group executes discharge to form 8 probes indicated by 2A, 2B, 2C, 2D, 2E, 2F, 2G and 2H in such a manner that they are aligned along a line, as shown in FIG. 7. Subsequently the discharges are executed by the third to fifth nozzle groups in a similar manner to form 40 probes (indicated by black dots) of the first column on the probe array 33.

In this operation, the center-to-center distance between the adjacent probes is 254 µm (corresponding to 100 dpi).

In this manner, the solutions of 40 kinds discharged from the first chip form probes of the first column on the probe array. The mode of such formation is schematically shown by 43 (for five probes 1A to 5A within such 40 probes) in FIG. 7.

Then the liquids are discharged from the second chip in a similar manner to form the probes of the second column (indicated by white circles) on the probe array.

The drive timing of the heaters is so adjusted that the probes of the first column formed by the first chip and those of the second column formed by the second chip have a center-to-center distance of 254 µm (corresponding to 100 dpi).

As in the case of first chip, the solutions of 40 kinds discharged from the second chip form probes of the second column on the probe array. The mode of such formation is schematically shown by 44 (for five probes 1C to 5C within such 40 probes) in FIG. 7.

Subsequently the liquids are discharged from the 3rd to 25th chips in a similar manner to form the probes (indicated by broken-lined circles) thereby completing the probe array.

As explained in the foregoing, the liquid discharge apparatus shown in FIG. 7 can produce a probe array bearing probes of 40 columns by 25 rows at a density of 100 dpi.

Also from the foregoing description, it will be easily understood that a probe array bearing a larger number of probes can be produced by a similar configuration.

In case of preparing a liquid discharge apparatus of one-dimensional configuration such as 1 row by 25 columns utilizing the semiconductor chip explained in the foregoing embodiment, the probe array can be produced by only the main scanning motion so that the probe array producing apparatus can be made simpler than that shown in FIG. 5.

Embodiments

In the following there will be explained embodiments of the present invention, with reference to the accompanying drawings.

(Embodiment 1)

Figure 2:
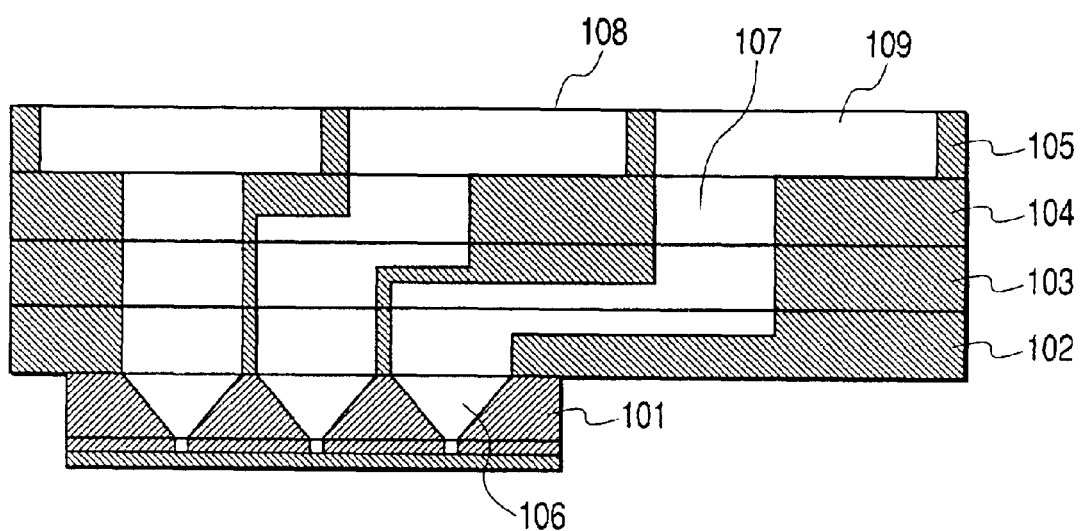
FIG. 2 is a cross-sectional view showing the principal part of the liquid discharge unit in a first embodiment of the present invention.

FIG. 1 is a view showing a liquid discharge apparatus (liquid discharge unit) for producing a probe array, constituting a first embodiment of the present invention, and FIG. 2 is a schematic cross-sectional view of a principal portion. The liquid discharge unit is composed of a heater board 101 constituted by a silicon substrate, and a liquid supply plate adjoined and laminated thereon.

The liquid supply plate has a laminar structure of plate members 102, 103, 104, 105 of alumina ceramics. The plate members 102, 103, 104 form a flow path 107 which communicates, at an end thereof, with a supply opening 106 formed by anisotropic etching on the upper face of the heater board 101, and at the other end, with a liquid reservoir 109 provided in the uppermost plate member 105 and constituting the liquid holding portion.

The uppermost plate member 105 is provided with the liquid reservoir 109 and a supply opening 108 corresponding to the opening thereof.

On the lower face of the heater board 101, nozzle openings (not shown) for discharging the probe solutions are arranged in a two-dimensional array, and each nozzle communicates with the supply opening 108 provided in the plate member 105 through the flow path 107 and the liquid reservoir 109.

Figure 3:
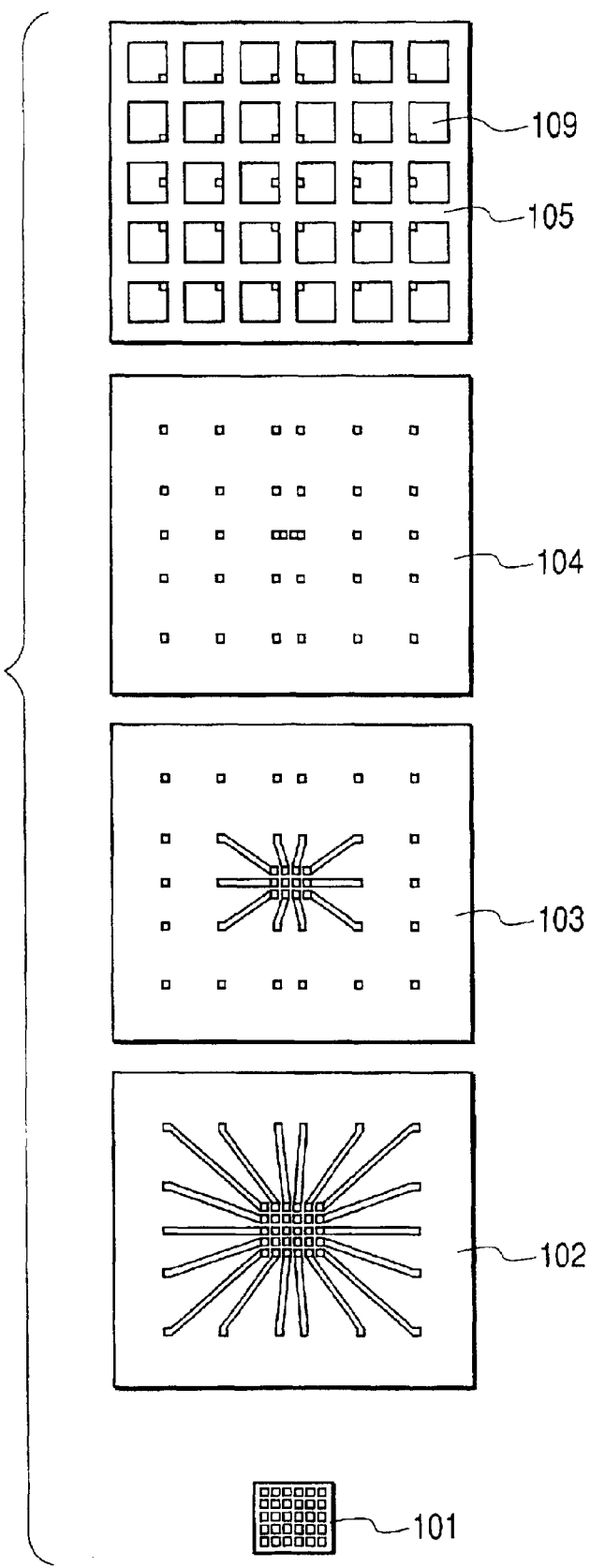
FIG. 3 is a view showing the arrangement of liquid flow paths in the components of the liquid discharge unit in the first embodiment of the present invention.

FIG. 3 shows the form of the liquid flow paths in the components. The probe solution is dropped, for example by a micropipette, into the supply opening 108 formed on the upper face of the plate member 105, and is retained in the flow path 108 and the liquid reservoir 109 by the capillary force of the nozzle. In the liquid reservoir 109, there may be placed a negative pressure generating member for generating a capillary force by the surface tension of the probe solution, for example a bundle of polypropylene fibers. Presence of such negative pressure generating member allows efficient intake of the probe solution into the liquid reservoir and more satisfactory discharge of the probe solution from the nozzle.

In order to prevent mutual mixing of the probe solutions dropped into the respective supply openings 108, the upper face (where the supply openings are provided) of the plate member 105 may be rendered water repellent.

Also, in order to achieve secure intake of the probe solution, dropped on the upper face of the liquid supply plate, into the supply opening 108, the upper face of the liquid supply plate may be provided with a groove continuous to the supply opening and enabling entry of the probe solution into the supply opening 108 by the capillary force.

In the present embodiment, a probe array can be advantageously produced for example by setting the arrangement pitch L2 of the nozzles to 100 μm and the arrangement pitch L1 of the liquid supply openings to 2.25 mm.

(Embodiment 2)

Figure 8:
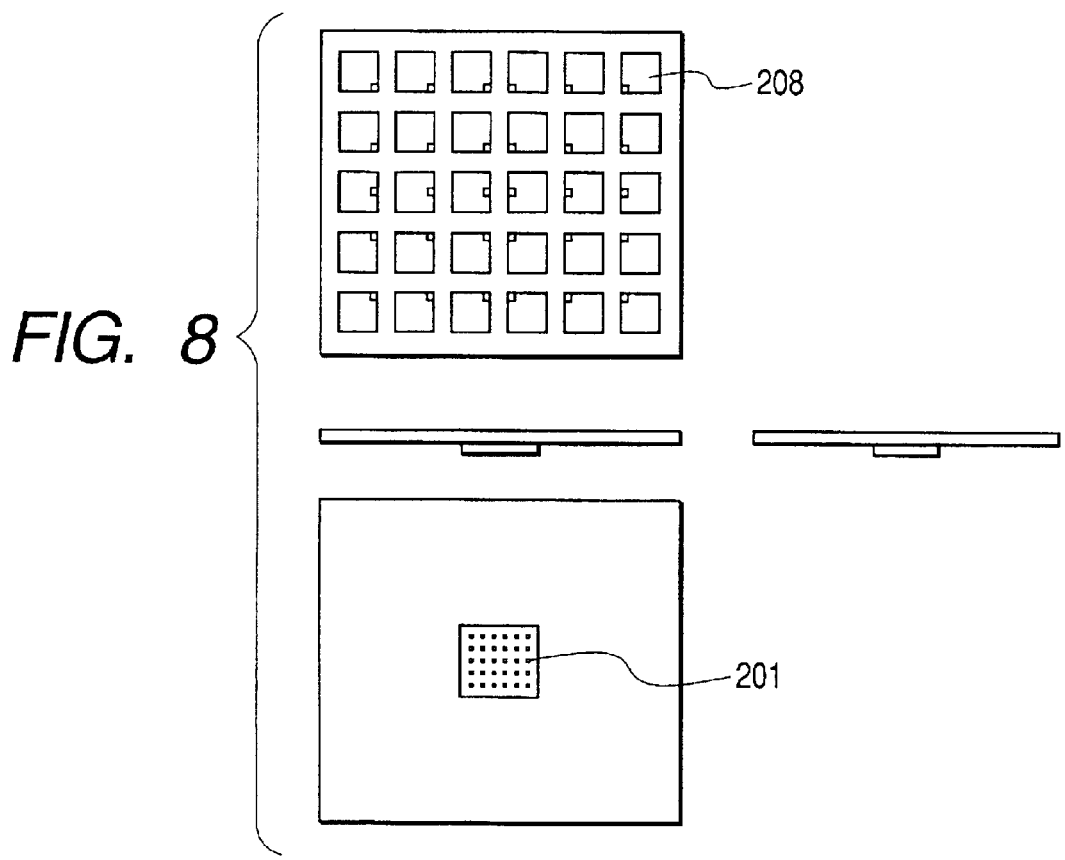
FIG. 8 is a view showing the liquid discharge unit in a second embodiment of the present invention.
Figure 9:
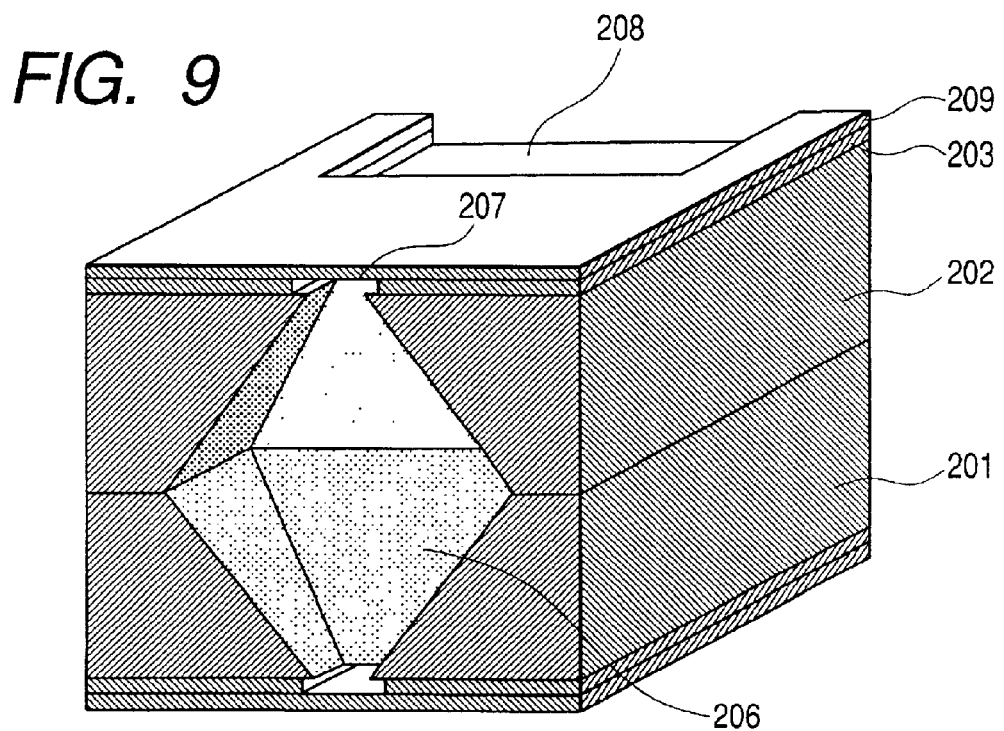
FIG. 9 is a perspective view of the liquid discharge unit of the second embodiment of the present invention, partially cut off for showing the cross section of the principal portion.

FIG. 8 is a view showing a liquid discharge unit for producing a probe array, constituting a second embodiment of the present invention, and FIG. 9 is a perspective view of the unit cut off in principal portion to show the cross section thereof. The liquid discharge unit of the present embodiment is composed of a heater board 201 constituted by a silicon substrate, and a liquid supply plate adjoined and laminated thereon.

On the lower face of the heater board 201, nozzle openings (not shown in FIG. 9) are arranged in a two-dimensional array.

The liquid supply plate is composed of a plate member 202 including a through hole constituting a part of the flow path connecting a supply opening 206, provided on the upper face of the heater board 201, and a supply opening 208, provided on the upper face of the liquid supply plate, and a resin layer 203 including a flow path 207 for connecting the through hole and the supply opening 208 and constituting a supply opening as an aperture.

The resin layer 203 is composed of a resinous material, such as ultraviolet-settable resin which can be patterned by a photolithographic process. The use of such material that can be patterned by the photolithographic process allows to form the flow path 207 photolithographically after the formation of the through hole in the plate member 202 by anisotropic etching. Stated differently, it is rendered possible to form the flow path 207 by the photolithographic process as an extension of the semiconductor process. As a result, it is easily possible to achieve fine structure and to attain complex arrangement of the flow paths as shown in FIG. 10.

Also, in order to increase the capacity of the liquid reservoir, a liquid reservoir plate for capacity increase may be adjoined on the upper face of the liquid supply plate.

Such reservoir plate for capacity increase may be formed from glass or by resin molding.

The probe solution is dropped for example by a micropipette into the supply opening 208 and is retained by the meniscus force of the nozzle. Also in this embodiment, a negative pressure generating member, for generating capillary force in the liquid reservoir by the surface tension of the probe solution, may be inserted in the liquid reservoir. In order to prevent mutual mixing of the probe solutions dropped into the respective supply openings, the upper face of the liquid supply plate may be rendered water repellent. Also, in order to achieve secure intake of the probe solution, dropped on the upper face of the liquid supply plate, into the supply opening 208, the upper face of the liquid supply plate may be provided with a groove continuous to the supply opening and enabling entry of the probe solution into the supply opening 208 by the capillary force.

(Embodiment 3)

Figure 12A:
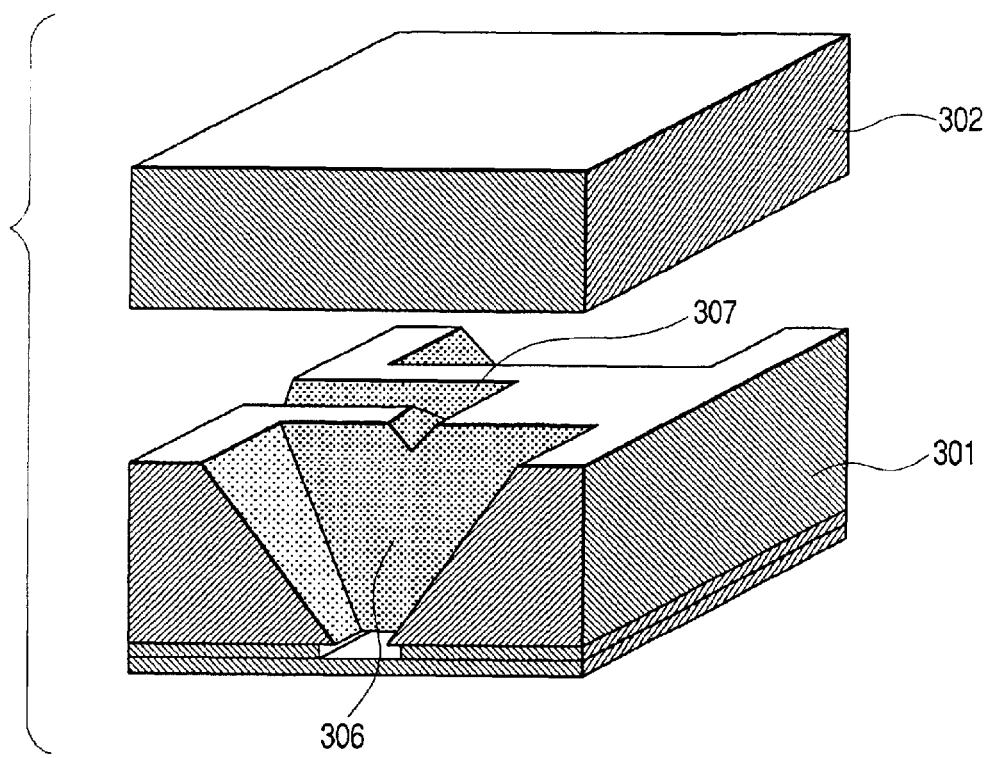
FIG. 12A is a perspective view of the liquid discharge unit of the third embodiment of the present invention, partially cut off for showing the cross section of the principal portion.
Figure 12B:
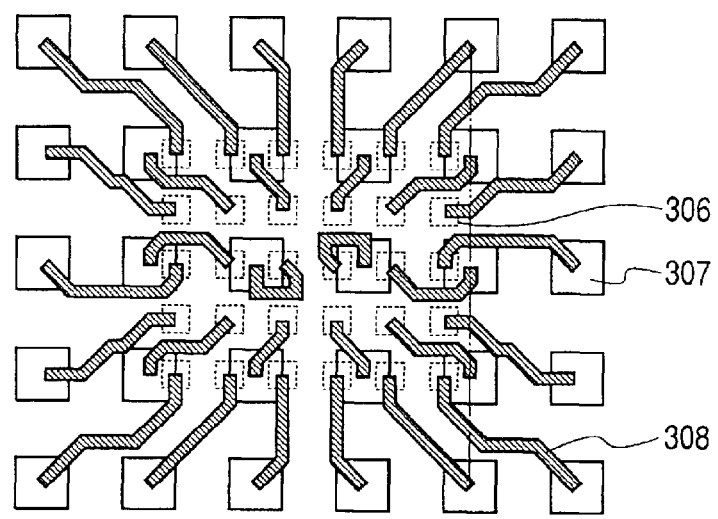
FIG. 12B is a see-through view showing the arrangement of the liquid flow paths in the liquid discharge unit of the third embodiment of the present invention.

FIG. 11 is a view showing a liquid discharge unit for producing a probe array, constituting a third embodiment of the present invention, while FIG. 12A is a perspective view of the unit cut off in principal portion to show the cross section thereof, and FIG. 12B is a see-through view showing the arrangement of flow paths.

The liquid discharge unit of the present embodiment is composed of a heater board 301 constituted by a silicon substrate, and a liquid supply plate. The heater board 301 is provided with supply openings 306 formed by anisotropic etching and liquid supply paths 307 formed by anisotropic etching and continuous to the supply openings 306, and is also provided, on the lower face thereof, with nozzle openings (not shown in FIG. 12A) for discharging probe solutions in a two-dimensional array. The liquid supply plate 302 is provided with liquid reservoirs and supply openings 308 constituting apertures thereof.

The probe solution is dropped for example by a micropipette into the supply opening 308 and is retained by the meniscus force of the nozzle. Also in this embodiment, a negative pressure generating member, for generating capillary force in the liquid reservoir by the surface tension of the probe solution, may be inserted in the liquid reservoir. In order to prevent mutual mixing of the probe solutions dropped into the respective supply openings, the upper face of the liquid supply plate may be rendered water repellent. Also, in order to achieve secure intake of the probe solution, dropped on the upper face of the liquid supply plate, into the supply opening 308, the upper face of the liquid supply plate may be provided with a groove continuous to the supply opening and enabling entry of the probe solution into the supply opening 308 by the capillary force.

(Embodiment 4)

FIG. 5 shows an example of the probe carrier producing apparatus utilizing the liquid discharge unit of the above-described configuration as liquid discharge means, wherein shown are a shaft 31 for guiding the substantially parallel movement of the liquid discharge unit 22, a stage 32 for supporting a carrier for producing the probe array, and a carrier 33 (for example a glass substrate) for forming the probe array.

The unit moves in the X-direction in FIG. 5 while the stage moves in the Y-direction, whereby the liquid discharge unit can move two-dimensionally with respect to the stage. FIG. 5 shows a configuration for fixing a glass substrate for constituting plural probe arrays and forming probes thereon, but it is also possible to produce probe arrays by supplying predetermined probe solutions to the wells of the carrier such as a large glass plate and then to cut such carrier into the individual probe arrays.

The liquid discharge unit is driven, while being moved relative to the substrate 33, so as to form the spots of the probe solutions according to the positional information of the probes on the probe array to be produced.

In case the arrangement of the nozzle openings in the liquid discharge unit coincides with that of the probes on the probe array, it is also possible to position the nozzle opening arrangement face of the liquid discharge unit opposed to the predetermined surface of the substrate, with alignment in a predetermined position, and to discharge the probe solutions without the scanning motion of the liquid discharge unit with respect to the substrate, thereby forming the spots of the probe solutions in the predetermined positions on the substrate.

In the probe carrier producing apparatus of the above-described configuration, the discharge energy generating means or the carrier supporting means of the liquid discharge apparatus may be controlled according to a control program provided in the producing apparatus or a command supplied from a host computer or the like provided outside the producing apparatus.

What is claimed is:

1. A liquid discharge apparatus for individually discharging probe liquids containing mutually different probes and producing a probe carrier bearing probes of plural kinds capable of specifically combining with a target substance and fixed in different positions on a carrier, the apparatus comprising:

a member having a pair of mutually opposed faces; and a liquid discharging portion, the number of which corresponds to the number of kinds of said probes, including:

1) a liquid holding portion for holding the probe liquid;

2) a supply opening for supplying the probe liquid to said liquid holding portion;

3) a liquid discharging nozzle for discharging the probe liquid; and 4) a flow path connecting said nozzle with said liquid holding portion, wherein a nozzle opening arrangement face, in which a plurality of openings of nozzles are arranged, is provided on one of the pair of mutually opposed faces of said member, a supply opening arrangement face, in which a plurality of liquid supply openings to said liquid holding portion are arranged, is provided on the other face of said member, and said flow path of each liquid discharging portion is provided as a path that passes through said member, wherein said member having said pair of mutually opposed faces has a laminated structure composed of a first plate-shaped member in which said nozzles are formed, and a second plate-shaped member in which said plurality of liquid supply opening are formed at a predetermined pitch of arrangement, and wherein the pitch of arrangement of the supply openings in said supply opening arrangement face is larger than the pitch of arrangement of the openings of the nozzles in said nozzle opening arrangement face.

2. The liquid discharge apparatus according to claim 1, wherein said liquid holding portion is formed in said second plate-shaped member.

3. The liquid discharge apparatus according to claim 2, wherein said liquid holding portions are formed in said second plate-shaped member.

4. The liquid discharge apparatus according to claim 1, wherein said plural nozzle openings are formed along a straight line or over vertical and lateral directions.

5. The liquid discharge apparatus according to claim 3, wherein said liquid holding portion is formed as a through hole penetrating said second plate-shaped member, an end of said through hole constitutes a connecting portion with said nozzle, and the other end constitutes an open end constituting said supply opening.

6. The liquid discharge apparatus according to claim 3, wherein said through hole is formed by a photolithographic process.

7. The liquid discharge apparatus according to claim 5, wherein the face bearing said supply openings is water repellent, in the periphery of each opening.

8. The liquid discharge apparatus according to claim 5, wherein the face bearing said supplying openings is provided with a groove communicating with each opening.

9. The liquid discharge apparatus according to claim 1, further comprising a liquid discharge energy generating element for liquid discharge from each of said nozzles.

10. The liquid discharge apparatus according to claim 9, wherein said liquid discharge energy generating element is a heater element for generating thermal energy to heat said probe solution thereby inducing film boiling therein and causing the resulting pressure to discharge the liquid from said discharge opening.

11. The liquid discharge apparatus according to claim 10, wherein said liquid discharging portion is provided with such a configuration that a bubble is generated in the probe solution at the discharge thereof from said nozzle by the activation of said heater element and said generated bubble communicates with the external air through said nozzle.

12. An apparatus for individually discharging probe liquids containing mutually different probes and producing a probe carrier bearing probes of plural kinds capable of specifically combining with a target substance and fixed in different positions on a carrier, the apparatus comprising:

A) a liquid discharge apparatus including:

a member having a pair of mutually opposed faces; and a liquid discharging portion, the number of which corresponds to the number of kinds of said probes, provided with;

1) a liquid holding portion for holding a the probe liquid;

2) a supply opening for supplying said liquid to the probe liquid holding portion;

3) a liquid discharging nozzle for discharging the probe liquid; and 4) a flow path connecting said nozzle with said liquid holding portion, wherein a nozzle opening arrangement face, in which a plurality of openings of nozzles are arranged, is provided on one of the pair of mutually opposed faces of said member, and a supply opening arrangement face in which a plurality of liquid supply openings to said liquid holding portion are arranged, is provided on the other face of said member, and said flow path of each liquid discharging portion is provided as a path that passes through said member, wherein said member having said pair of mutually opposed faces has a laminated structure composed of a first plate-shaped member in which said nozzles are formed, and a second plate-shaped member in which said plurality of liquid supply opening are formed at a predetermined pitch of arrangement, and wherein the pitch of arrangement of the supply openings in said supply opening arrangement face is larger than the pitch of arrangement of the openings of the nozzles in said nozzle opening arrangement face; and B) aligning means for aligning the relative position of said carrier and said liquid discharge apparatus.

13. A method for producing a probe carrier bearing probes of plural kinds capable of specifically combining with a target substance and fixed in different positions on a carrier, the method comprising:

A) a step of preparing a liquid discharge apparatus for individually discharging probe liquids containing mutually different probes, the apparatus including:

a member having a pair of mutually opposed faces; and a liquid discharging portion, the number of which corresponds to at least the number of kinds of the probes, provided with 1) a liquid holding portion for holding the probe liquid;

2) a supply opening for supplying the probe liquid to said liquid holding portion;

3) a liquid discharging nozzle for discharging the probe liquid; and 4) a flow path connecting said nozzle with said liquid holding portion, wherein a nozzle opening arrangement face, in which a plurality of openings of nozzles are arranged, is provided on one of the pair of mutually opposed faces of said member, a supply opening arrangement face, in which a plurality of liquid supply openings to said liquid holding portion are arranged, is provided on the other face of said member, and said flow path of each liquid discharging portion is provided as a path that passes through said member, wherein said member having said pair of mutually opposed faces has a laminated structure composed of a first plate-shaped member in which said nozzles are formed, and a second plate-shaped member in which said plurality of liquid supply opening are formed at a predetermined pitch of arrangement, and wherein the pitch of arrangement of the supply openings in said supply opening arrangement face is larger than the pitch of arrangement of the openings of the nozzles in said nozzle opening arrangement face; and B) a step of discharging said liquid containing said probe onto the different positions on said carrier from said liquid discharge apparatus.

* * * * *

UNITED STATES PATENT AND TRADEMARK OFFICE
CERTIFICATE OF CORRECTION

PATENT NO. : 6,830,621 B2
DATED : December 14, 2004
INVENTOR(S) : Kenta Udagawa et al.

It is certified that error appears in the above-identified patent and that said Letters Patent is hereby corrected as shown below:

Column 1,
Line 56, "DNA's" should read -- DNAs --.

Column 3,
Line 14, "EPO 703 825B1" should read -- EP 0 703 825 B1 --.

Column 5,
Line 44, "with;" should read -- with --.

Column 6,
Line 14, "with;" should read -- with --.

Column 9,
Line 3, "structures" should read -- structure, --.

Column 11,
Line 29, "Particularly is" should read -- Particularly in --.

Column 20,
Line 5, "opening" should read -- openings --;
Line 59, "with;" should read -- with --; and
Line 60, "holding a the probe" should read -- holding the probe --.

Column 21,
Line 14, "opening" should read -- openings --; and
Line 32, "with" should read -- with: --.

Signed and Sealed this

Thirty-first Day of May, 2005

JON W. DUDAS
*Director of the United States Patent and Trademark Office*